(12) United States Patent
Gonzalvez et al.

(10) Patent No.: US 9,345,497 B2
(45) Date of Patent: May 24, 2016

(54) JIG FOR PLACING A SHOULDER PROSTHESIS JOINT IMPLANT ON A HUMERAL HEAD

(71) Applicant: ASTON MEDICAL, Saint-Etienne (FR)

(72) Inventors: Martin Gonzalvez, Dijon (FR); Pierre Trouilloud, Dijon (FR); Michel Colombier, Montpellier (FR)

(73) Assignee: Aston Medical, Saint-Etienne (FR)

( * ) Notice: Subject to any disclaimer, the term of this patent is extended or adjusted under 35 U.S.C. 154(b) by 82 days.

(21) Appl. No.: 14/062,972

(22) Filed: Oct. 25, 2013

(65) Prior Publication Data

US 2014/0171953 A1 Jun. 19, 2014

(30) Foreign Application Priority Data

Oct. 26, 2012 (FR) ...................................... 12 60203

(51) Int. Cl.
*A61F 5/00* (2006.01)
*A61B 17/17* (2006.01)
*A61B 17/15* (2006.01)
*A61B 17/00* (2006.01)

(52) U.S. Cl.
CPC ......... *A61B 17/1739* (2013.01); *A61B 17/1703* (2013.01); *A61B 17/15* (2013.01); *A61B 17/1725* (2013.01); *A61B 2017/0042* (2013.01); *A61B 2017/1778* (2013.01)

(58) Field of Classification Search
CPC .. A61B 75/15; A61B 17/1739; A61B 17/175; A61B 2017/1778; A61B 2017/0042; A61F 2/40

USPC ....................................................... 623/19.14
See application file for complete search history.

(56) References Cited

U.S. PATENT DOCUMENTS

| | | | |
|---|---|---|---|
| 2008/0172054 A1* | 7/2008 | Claypool et al. ................ | 606/87 |
| 2009/0254093 A1* | 10/2009 | White et al. .................... | 606/89 |
| 2009/0264889 A1 | 10/2009 | Long et al. | |
| 2012/0041446 A1* | 2/2012 | Wong et al. ..................... | 606/96 |
| 2012/0143267 A1 | 6/2012 | Iannotti et al. | |
| 2012/0245647 A1* | 9/2012 | Kunz et al. .................. | 606/86 R |
| 2012/0296339 A1* | 11/2012 | Iannotti et al. .................. | 606/87 |

FOREIGN PATENT DOCUMENTS

| | | |
|---|---|---|
| FR | 2967047 A1 | 5/2012 |
| WO | 2012/021241 A2 | 2/2012 |

OTHER PUBLICATIONS

French Search Report for priority French Application No. 1260203, dated Apr. 12, 2013.

\* cited by examiner

*Primary Examiner* — Kevin T Truong
*Assistant Examiner* — Si Ming Ku
(74) *Attorney, Agent, or Firm* — Heslin Rothenberg Farley & Mesiti P.C.

(57) ABSTRACT

The jig is formed based on a three-dimensional reconstruction of the bone elements of the joint from tomodensitometric data; the marking of points on the humerus being used as a basis for the positioning of the considered prosthetic element. The jig includes: a support base cooperating with the humeral head according to a single position, one portion of the base cooperating with the intertubercular sulcus or bicipital groove; a gripping portion; and a breakable area temporarily receiving a cutting block to allow its fixation to the humeral bone before enabling to perform the humeral resection.

10 Claims, 6 Drawing Sheets

Figure 1:
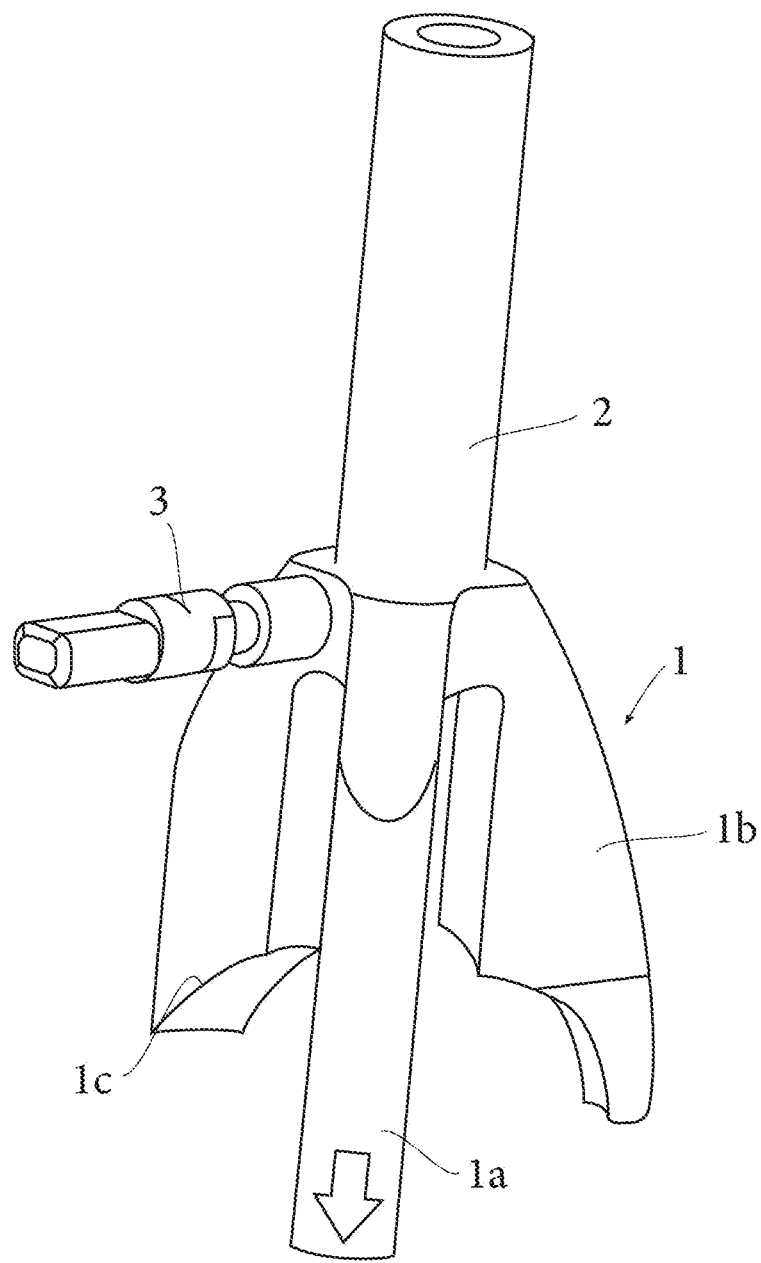

EM: medial epicondyle
EL: lateral epicondyle
AT: top of the humeral head
PB: low point of the humeral head
CT: center of the humeral head

JIG FOR PLACING A SHOULDER PROSTHESIS JOINT IMPLANT ON A HUMERAL HEAD

CROSS REFERENCE TO RELATED APPLICATION

This application claims priority of French application No. 1260203 filed Oct. 26, 2012, the entire contents of which is hereby incorporated by reference herein.

BACKGROUND ART

The invention relates to the technical field of single-use instruments customized for the patient for the installation of orthopedic implants, especially for a prosthesis of the shoulder joint.

More specifically, the invention relates to a customized humeral jig for the installation of a shoulder prosthesis, especially of reverse type.

It should be reminded that "reverse shoulder joint prosthesis" designates a prosthesis having its hemispherical condyle, as such, attached at the level of the glenoid cavity to cooperate with a cup or platen of complementary shape, and fixed on a humeral stem. In other words, in this type of prosthesis, the glenoid implant comprises a hemispherical condyle while the humeral implant comprises a cup or platen.

It is now admitted that the fixing and the positioning of prosthetic implants are particularly important for the success of the biomechanical operation of the shoulder prosthesis and its lifetime.

An advantageous solution for the installation of a shoulder prosthesis comes out from the teachings of document FR 2967047 also assigned to the applicant hereof.

This document relates to a jig for installing a shoulder prosthesis on a glenoid cavity by planning in 3 dimensions the installation of the implant based on scanner or RMI images.

The 2D images are processed by means of specific software enabling to segment the bone areas of interest for the installation, with the purpose of reconstructing a three-dimensional structure. Landmarks enabling to determine a specific coordinate system in the scapular bone are defined on this structure in the case of the previously-mentioned document.

This three-dimensional model enables to accurately simulate, plan, and measure the orientation of the prosthetic implant according to the previously-mentioned coordinate system.

The operator plans not only the size and the positions of the considered implant, but also compares in the 3 planes of space the joint geometry with and without a prosthesis according to the selected elements.

In other words, the desired aim is to form an installation jig customized for the patient, which enables to reconstruct on the patient the simulation performed by means of the planning software.

Based on the state of the art defined by the teachings of document FR 2967047, the problem that the present invention aims at solving is to form a customized installation jig in the case of a humeral implant.

BRIEF SUMMARY OF THE INVENTION

According to the invention, the jig for placing a shoulder prosthesis joint implant on a humeral head is characterized in that it has:

a support base cooperating with the humeral head according to a single position and having one of its portions cooperating with the intertubercular sulcus or bicipital groove, a portion forming gripping means, a breakable area capable of temporarily receiving a cutting block to enable its fixation to the humeral bone before enabling to perform the humeral resection.

The use of the lateral bicipital groove appears to be particularly important and advantageous for the positioning of the jig, while forming a single area, easy to locate, for the operator.

Based on this basic design, in an embodiment, the support base and the portion forming the gripping means are made in a single block. Advantageously, the support base forms a tripod with three legs, one of which cooperates with the lateral bicipital groove.

In another embodiment, one at least of the legs is jointed.

According to another feature, the breakable area receiving the cutting block is arranged between the leg cooperating with the lateral bicipital groove and one of the two other legs. The breakable area is oriented angularly with respect to the leg cooperating with the lateral bicipital groove and substantially perpendicularly with respect to the portion forming the gripping means.

As comes out of the teachings of previously-mentioned patent application FR 2967047, the installation jig according to the invention results from the 3D peroperative planning based on a three-dimensional reconstruction of the humerus based on tomodensitometric data and on the marking of points on the epiphyseal head of the humerus, said points being projected, on the one hand, in a plane normal to the diaphyseal axis and tangent to the humeral head and, on the other hand, in a plane perpendicular to the previous one and containing certain points in order to calculate the retroversion of the humerus.

Advantageously, the points located on the humerus are the medial epicondyle, the lateral epicondyle, the top of the humeral head, the low point of the humeral head, and the center of the humeral head.

As indicated, the present invention is particularly advantageous in the case of a reverse shoulder joint prosthesis.

BRIEF DESCRIPTION OF THE DRAWING FIGURES

Figure 2:
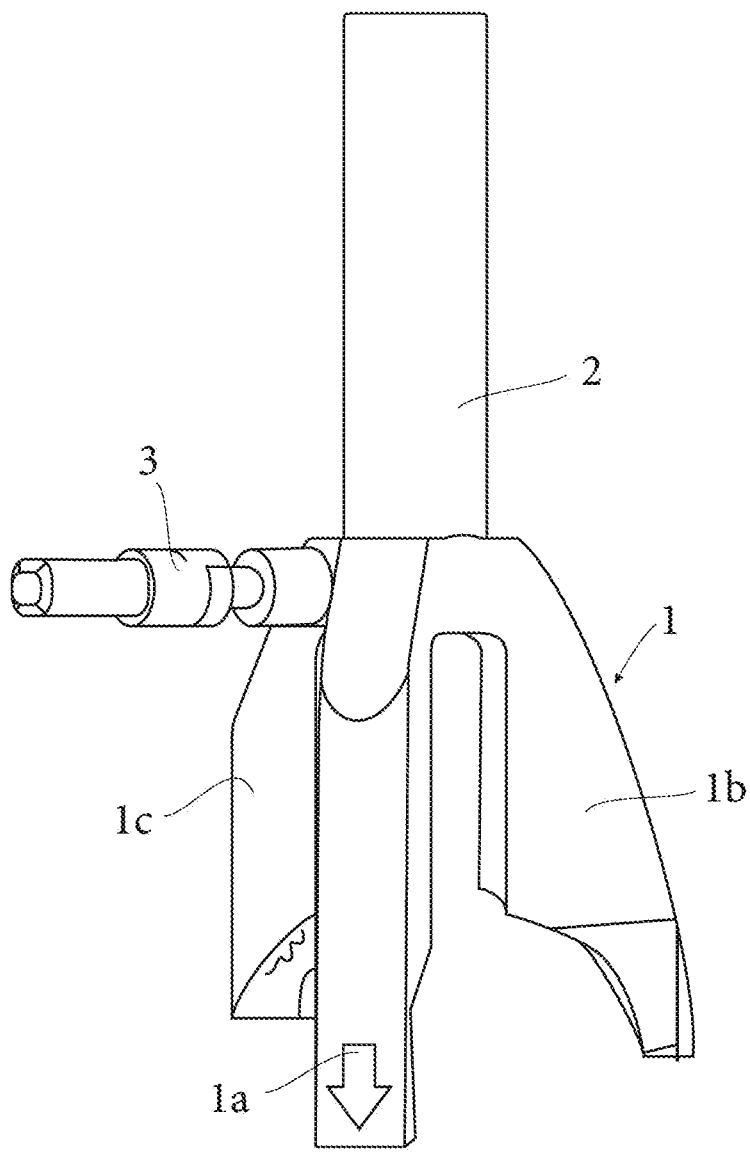
Figure 3:
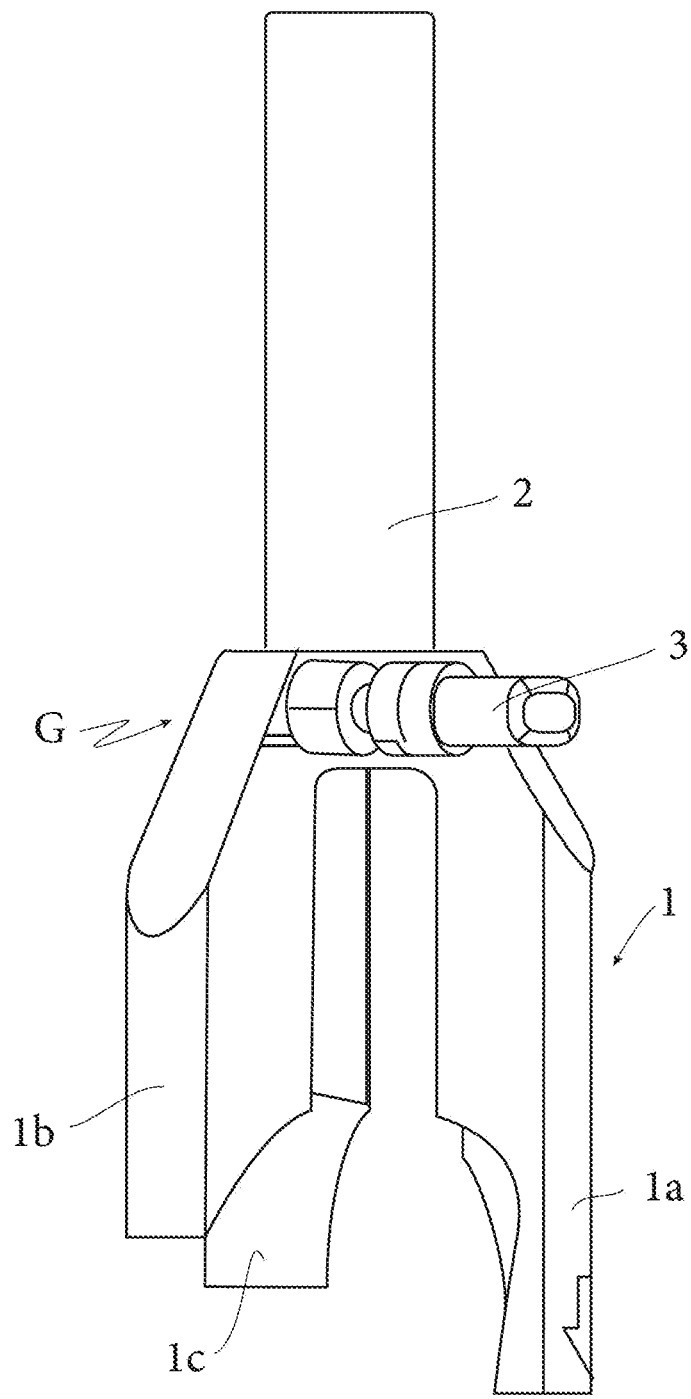
Figure 4:
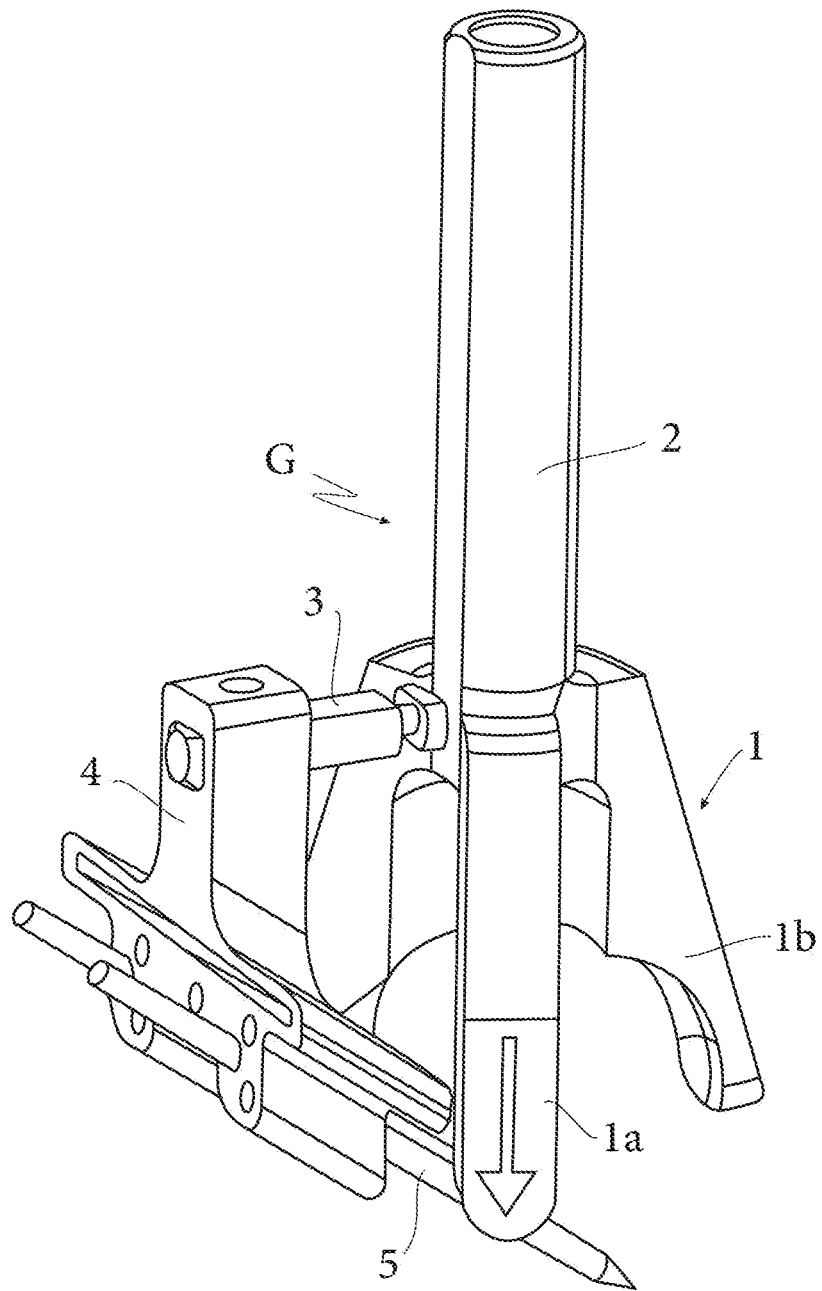
Figure 7:
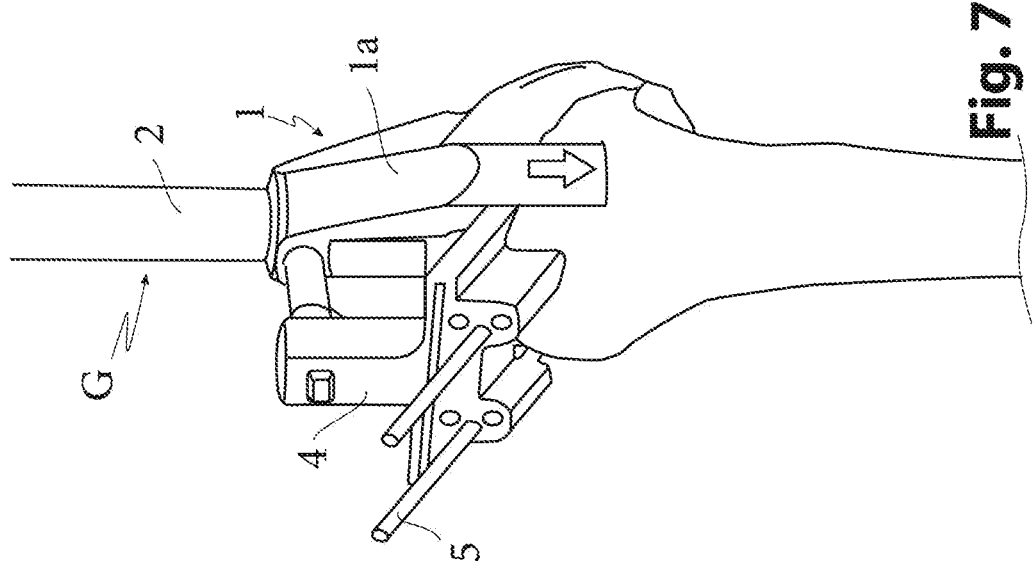
Figure 6:
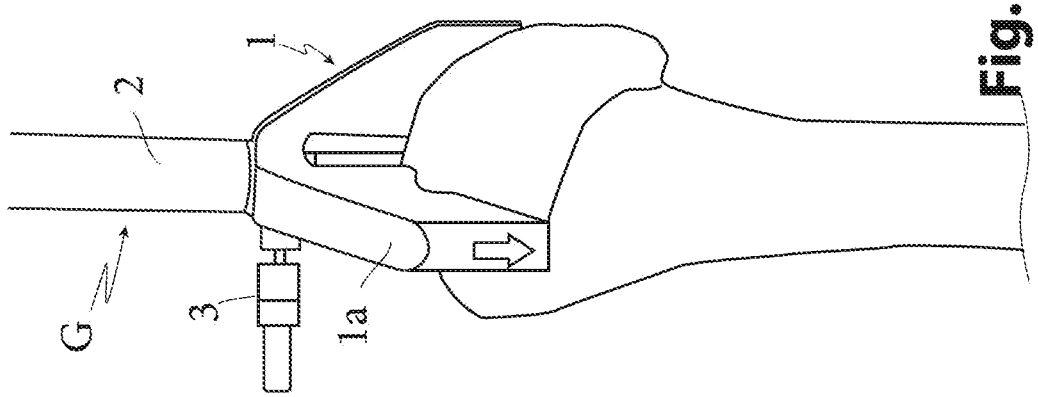
Figure 5:
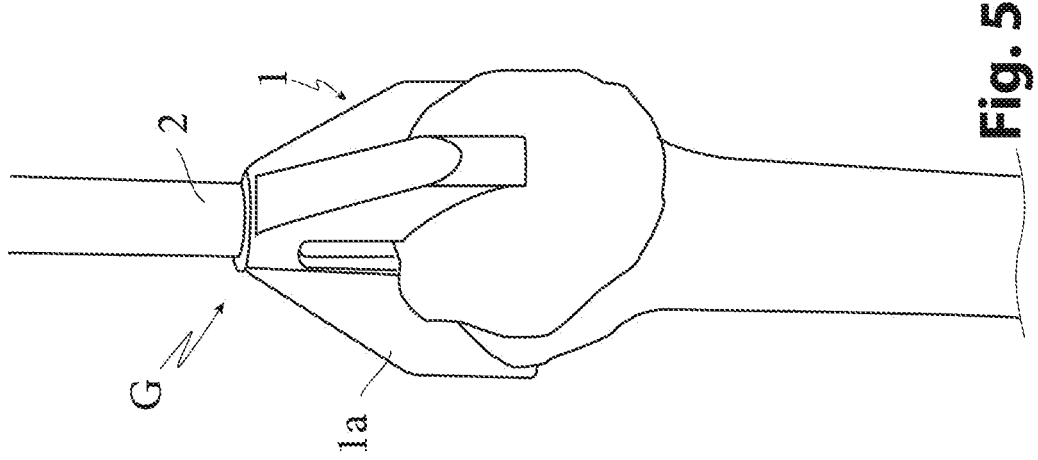
Figure 8:
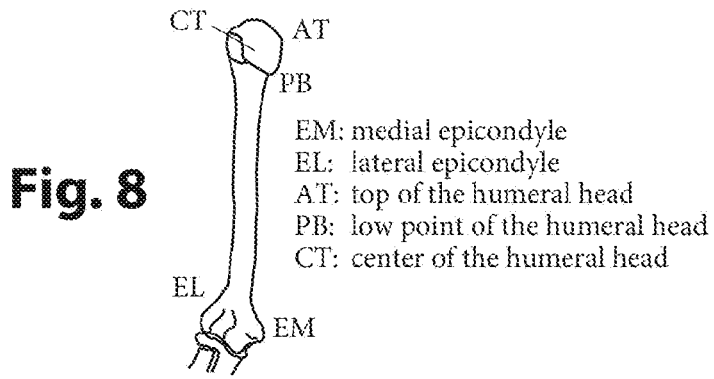
Figure 9:
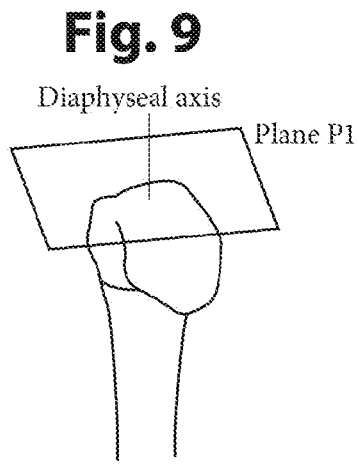
Figure 10:
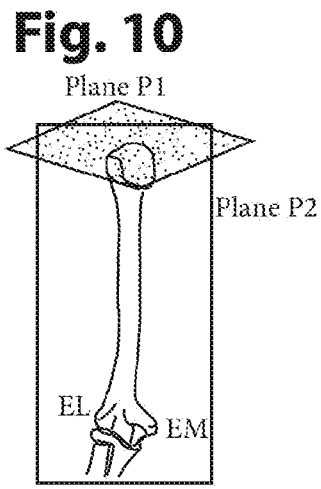
Figure 11:
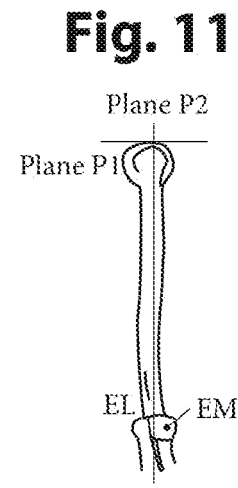
Figure 12:
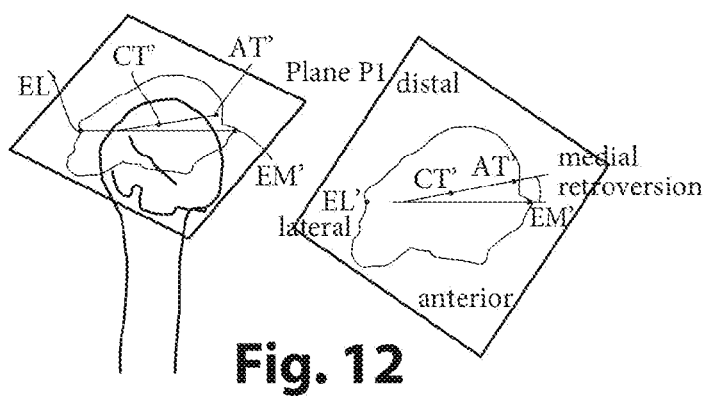
Figure 13:
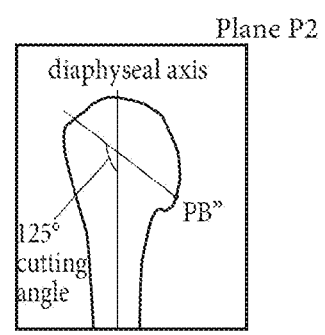

The invention is discussed hereafter in further detail by means of the appended drawings, among which:

FIGS. 1 to 3 are perspective views according to different directions of the humeral installation jig, FIG. 4 is a perspective view of the installation jig fitted with a cutting guide and with its fixation nails, FIGS. 5 and 6 are perspective views showing the positioning of the jig at the level of the humeral head, FIG. 7 is a perspective view corresponding to FIG. 6 after installation of the cutting jig, FIG. 8 shows the landmarks on the humerus, FIGS. 9, 10, and 11 show the definition of the humeral planes, FIG. 12 shows the natural retroversion of the humerus, FIG. 13 shows the determination of the humeral cutting level.

DETAILED DESCRIPTION

As indicated, the customized humeral installation jig is based on a three-dimensional reconstruction of the bone elements of the joint based on tomodensitometric data, the marking of points on the humerus being used as a basis for the positioning of the considered prosthetic element.

Reference should be made to FIG. 8 which shows the landmarks on the humerus. (EM) corresponds to the medial epicondyle, (EL) corresponds to the lateral epicondyle, (AT) corresponds to the top of the humeral head, (PB) corresponds to the low point of the humeral head, and (CT) corresponds to the center of the humeral head.

FIGS. 9, 10, and 11 show the definition of the humeral planes, that is, a plane (P1) normal to the diaphyseal axis and tangent to the humeral head and a plane (P2) perpendicular to (P1) and containing (EL) and (EM).

The natural retroversion of the humerus results from the projection of points EM, EL, CT, AT in plane P1, that is, points EM', EL', CT', AT' (FIG. 12).

The determination of the humeral cutting plane is defined by (PB") whichresults from the projection of point (PB) in plane (P2).

On a humeral planning screen, the operator views a humeral stem in so-called "0" position corresponding to a 125° humeral resection, running through the lowest point of the humeral head and having no retroversion or anteversion.

The humeral implant is also, by default, in neutral position.

The operator can successively set the size of the stem, the size and the position of the humeral element, as well as the retroversion and the height of the humeral cut.

A mathematical approach of the relative position of the bone assembly is then performed with respect to the planned prosthetic assembly. On this regard, the screen provides a spacing in the 3 planes between the position of the planned joint center (glenoid cavity) and the prosthesis joint center (center of the humeral head), the screen also gives the lateralization difference of the humerus between its initial position and its planned position, which results from an analysis performed with a default standard insert.

It is possible for the operator to modify this lateralization by varying the thickness of the insert.

According to the invention, the customized humeral installation jig is formed based on this planning, thus enabling to peroperatively reproduce on the patient the plan virtually achieved with the planning software.

The customized installation jig generally designated as (G) comprises a support base (1) cooperating with the humeral head according to a single customized position.

In an embodiment, the support base (1) forms a tripod and thus has 3 angularly-shifted legs (1a), (1b), and (1c), one of the legs (1a), designed with a marking such as the arrow illustrated in the drawing Figures, cooperating with the bicipital groove of the humeral head to form a single landmark for the operator.

The jig (G) comprises gripping means (2).

In an embodiment, the support base (1) and the portion (2) forming the gripping means are formed in a single block, as in the appended drawings.

Another embodiment according to which one at least of the legs of the support base (1) is jointed with respect to portion (2) is not excluded. Portion (2) appears in the form of a handle which may have an axial bore for the installation of an intramedullary stem in the case where it is difficult to install the jig on the humeral head.

Substantially at the level of the connection of the support base (1) to the gripping handle (2), the jig comprises a breakable portion or area (3) capable of temporarily receiving a cutting block or guide (4) for allowing its fixation to the humeral bone before enabling to perform the humeral resection.

The breakable area (3) is arranged between the leg (1a) cooperating with the bicipital groove and one of the other legs (1b) or (1c).

This breakable area (3) is oriented angularly with respect to the leg (1a) and substantially perpendicularly to the portion forming the gripping means (2).

After exposure of the humeral head, the humeral installation jig according to the invention is placed before any act on osteophytes in a single position due to the leg (1a) which cooperates with the bicipital groove.

The cutting block (4) is arranged on the breakable area (3) so as to abut against the jig, whereby it is automatically positioned in terms of height and orientation.

The cutting guide can then be fixed, for example, by means of nails (5) engaged in the cortical substance of the humeral head. After fixation of the cutting block, it is possible to remove the installation jig by breaking it at the level of the breakable area (3), which is then removed from the cutting block.

In the illustrated embodiment, the breakable area (3) is formed by a circular bearing whereon a portion of the cutting guide can be freely engaged.

The breakable area as such results from a thinning of the section of the circular bearing at the level of its connection with the installation guide.

After having removed the jig and leaving in place the cutting guide as indicated, it is possible to perform the humeral resection in the position planned by means of the planning software and peroperatively reproduced by the customized jig (G).

Advantageously, the humeral installation jig according to the invention replaces the intramedullary stem for positioning the cutting guide according to the prior state of the art.

In an alternative embodiment, the jig and the cutting guide may be a single block to form a disposable single-use assembly.

The advantages well appear from the disclosure.

The invention claimed is:

1. An installation jig for placing a shoulder prosthesis joint implant on a humeral head, said jig being formed based on a three-dimensional reconstruction of bone elements of the joint from tomodensitometric data, marking of points on the humerus being used as a basis for the positioning of the implant, the jig comprising:
 a support base comprising a tripod having three legs extending downwardly from an upper portion, the tripod being adapted to cooperate with the humeral head according to a single position, one leg of said tripod being designated for cooperating with an intertubercular sulcus or bicipital groove,
 a gripping portion extending upwardly from the upper portion of the tripod, and
 a bearing member arranged between said one leg and another of the legs and extending laterally outward from the upper portion of the tripod, the bearing member including a breakable area, configured to be readily broken, the bearing member being configured to temporarily support a cutting block to allow cutting block fixation to the humeral head followed by separation and removal of the installation jig from the cutting block by breaking of the breakable area before enabling to perform a humeral resection.

2. The installation jig of claim 1, wherein the support base and the gripping portion comprise a single block.

3. The installation jig of claim 1, wherein at least one of the legs is jointed.

4. The installation jig of claim 1, wherein the breakable area is oriented angularly with respect to the one leg and substantially perpendicularly with respect to the gripping portion.

5. The installation jig of claim 1, wherein the breakable area comprises a thinned section of the bearing member.

6. The installation jig of claim 1, wherein the gripping portion comprises a handle having an axial bore for installation of an intramedullary stem.

7. The installation jig of claim 1 in combination with the cutting block, the cutting block including means for temporarily receiving the bearing member and means for affixing the cutting block to the humeral head.

8. The combination of claim 7, wherein the means for affixing comprises nails.

9. The installation jig of claim 1, wherein said one leg of said tripod is designated with a marking for cooperating with the intertubercular sulcus or bicipital groove.

10. A method for placing a shoulder prosthesis joint implant on a humeral head, comprising the steps of:
   providing the installation jig of claim 1,
   placing the support base on the humeral head, with the one leg of the tripod designated with a marking aligned with the intertubercular sulcus or the bicipital groove,
   temporarily mounting the cutting block on the bearing member,
   fixating the cutting block to the humeral head,
   separating and removing the installation jig from the cutting block by breaking of the breakable area, and
   performing a humeral resection using the fixated cutting block.

\* \* \* \* \*